US00PP32001P2

(12) United States Plant Patent
Malinowski et al.

(10) Patent No.: US PP32,001 P2
(45) Date of Patent: Jul. 21, 2020

(54) ***HIBISCUS* PLANT NAMED '15173 GR'**

(50) Latin Name: ***Hibiscus* hybrid (L.)**
Varietal Denomination: 15173 GR

(71) Applicant: The Texas A&M University System, College Station, TX (US)

(72) Inventors: Dariusz P. Malinowski, Vernon, TX (US); William E. Pinchak, Vernon, TX (US); R. Steve Brown, Vernon, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 16/501,692

(22) Filed: May 22, 2019

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608; A01H 5/02
See application file for complete search history.

(56) References Cited

PUBLICATIONS

U.S. Appl. No. 16/501,691, filed May 22, 2019, Malinowski et al.
U.S. Appl. No. 16/501,696, filed May 22, 2019, Malinowski et al.
U.S. Appl. No. 16/501,694, filed May 22, 2019, Malinowski et al.
U.S. Appl. No. 16/501,693, filed May 22, 2019, Malinowski et al.
U.S. Appl. No. 16/501,695, filed May 22, 2019, Malinowski et al.
U.S. Appl. No. 16/501,698, filed May 22, 2019, Malinowski et al.
U.S. Appl. No. 16/501,697, filed May 22, 2019, Malinowski et al.
"Hardy *Hibiscus* 'Texas Star'," Denton County Master Gardner Association, <https://dcmga.com/north-texas-gardening/perennials/master-gardener-favorites/texas-star-hibiscus/>, accessed on Aug. 26, 2019.

*Primary Examiner* — Keith O. Robinson
(74) *Attorney, Agent, or Firm* — Dentons US LLP

(57) ABSTRACT

'15173 GR' is a new and distinct hardy herbaceous *Hibiscus* hybrid with novel characteristics that include upright branched stems, numerous, outward-facing, flowers that exhibit a background that is between moderate yellowish pink and strong pink in the mid and upper part, and between vivid reddish orange and deep yellowish pink from the middle part down to the edge of the center eye, a strong red center eye, a prolonged blooming season, and hastate, tri-lobed leaves.

5 Drawing Sheets

Latin name of the genus and species of the plant claimed: *Hibiscus* hybrid (L.).

Cultivar denomination: '15173 GR'.

BACKGROUND OF THE INVENTION

The present invention relates to the new and distinct *hibiscus* plant '15173 GR'. '15173 GR' was generated from a cross performed on Jul. 12, 2014 near Vernon, Tex. between '10543-3' (pod parent, unpatented) and '14054-3' (pollen parent, unpatented). The pedigrees of each parent reflect a complex mixture of *hibiscus* species that include, for example, *H. mocheutos, H. coccineus, H. militaris*, or *H. dasycalyx*. The seed from this cross was harvested on Aug. 25, 2014 and the '15173 GR' seedling was selected in the summer of 2015. '15173 GR' was first asexually propagated near Vernon, Tex. in 2016 by stem tip cuttings. The resulting as well as subsequent asexually propagated plants have been stable and true to type throughout successive generations.

SUMMARY OF THE INVENTION

'15173 GR' differs from its parents and all other known hardy herbaceous *hibiscus* plants. The following are the most outstanding and distinguishing characteristics of '15173 GR': (1) it is a hardy perennial with dense branching and a compact growth habit; (2) it blooms profusely over a prolonged season; and (3) its flowers exhibit a background that is between moderate yellowish pink (RHS 38B) and strong pink (RHS 52D) in the mid and upper part, and between vivid reddish orange (RHS 44C) and deep yellowish pink (RHS 44D) from the middle part down to the edge of the center eye, which is strong red (RHS 46A).

'15173 GR' plants can be readily and unambiguously distinguished from those of its parents. '15173 GR' plants exhibit flowers that are between moderate yellowish pink (RHS 38B) and strong pink (RHS 52D) in the mid and upper part, and between vivid reddish orange (RHS 44C) and deep yellowish pink (RHS 44D) from the middle part down to the edge of the center eye and that have an average diameter of 17 cm and trilobed, hastate leaves with slightly indented margins. Whereas, '10543-3' plants (pod parent) exhibit vivid purplish pink (RHS 61D) flowers that have an average diameter of 25 cm and lobed leaves with deeply indented margins; and '14054-3' plants (pollen parent) exhibit very pale purplish-blue (RHS 97C) flowers that have an average diameter of 16 cm and hastate leaves with slightly indented margins.

*H. coccineus* (unpatented), also known as Texas Star *hibiscus* or scarlet rose *hibiscus* and is within the pedigree of '15173 GR', is the *hibiscus* plant that exhibits flowers with a shape that is most similar to those of '15173 GR'. Nonetheless, plants of '15173 GR' and *H. coccineus* can also be readily and unambiguously distinguished from one another at least based upon growth habit, flowering time, flowering amount, and flower shape. '15173 GR' plants exhibit wider petals, a more compact growth habit, and earlier and more profuse flowering than *H. coccineus* plants.

BRIEF DESCRIPTION OF THE DRAWINGS

'15173 GR' is illustrated by the accompanying photographs, which show the plant's form, foliage, flowers, and leaves. The colors shown are as true as can be reasonably obtained by conventional photographic procedures.

DETAILED BOTANICAL DESCRIPTION

Figure 1:
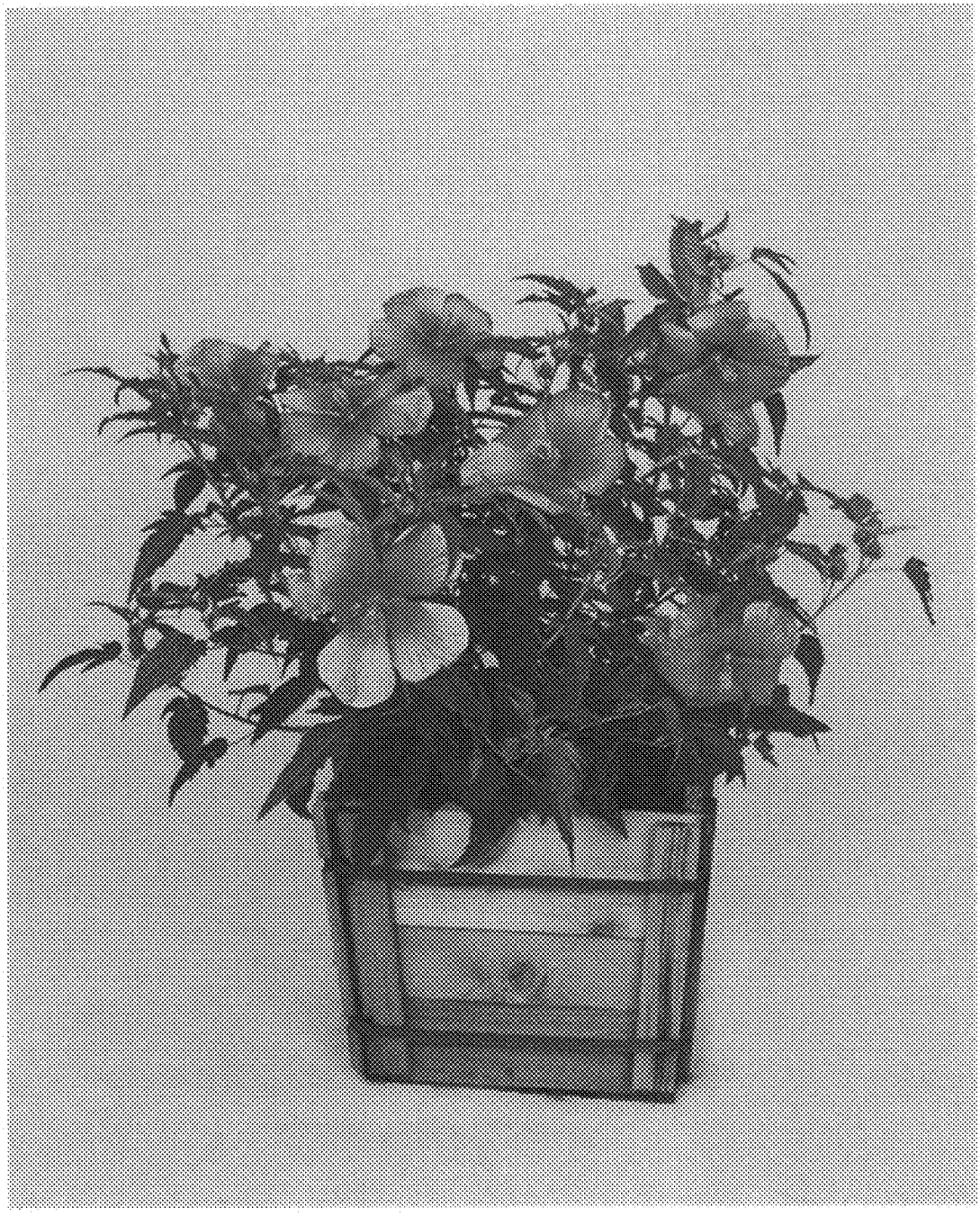
FIG. 1—Shows a 6-week-old '15173 GR' plant in a container.
Figure 2:
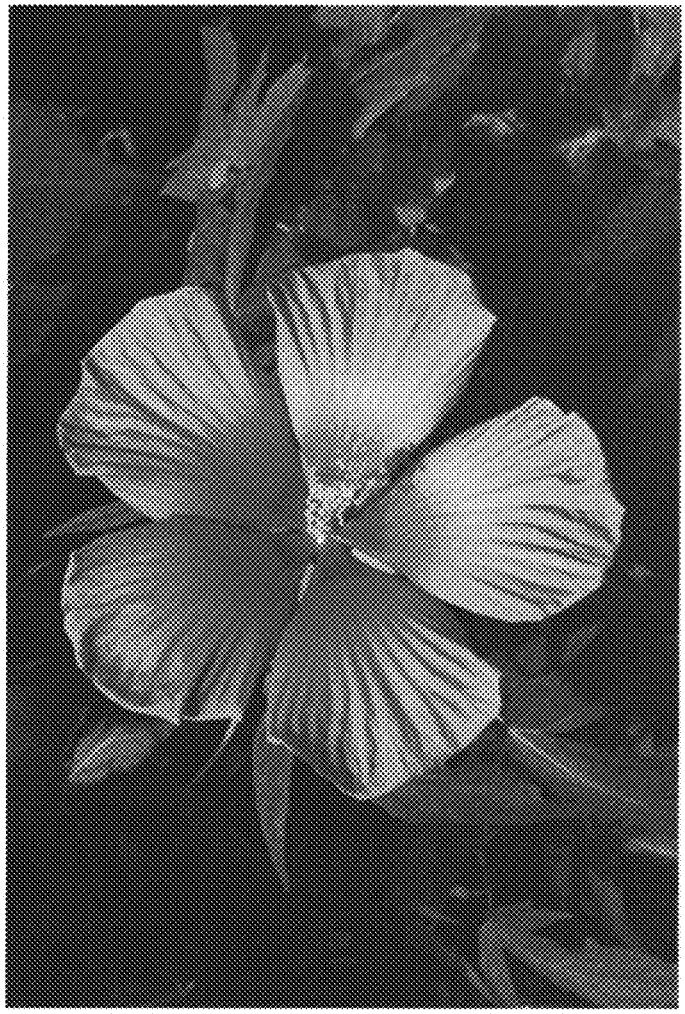
FIG. 2—Shows a '15173 GR' flower as seen looking slightly askew from the adaxial surface of the petals on a 2-year-old plant.
Figure 3:
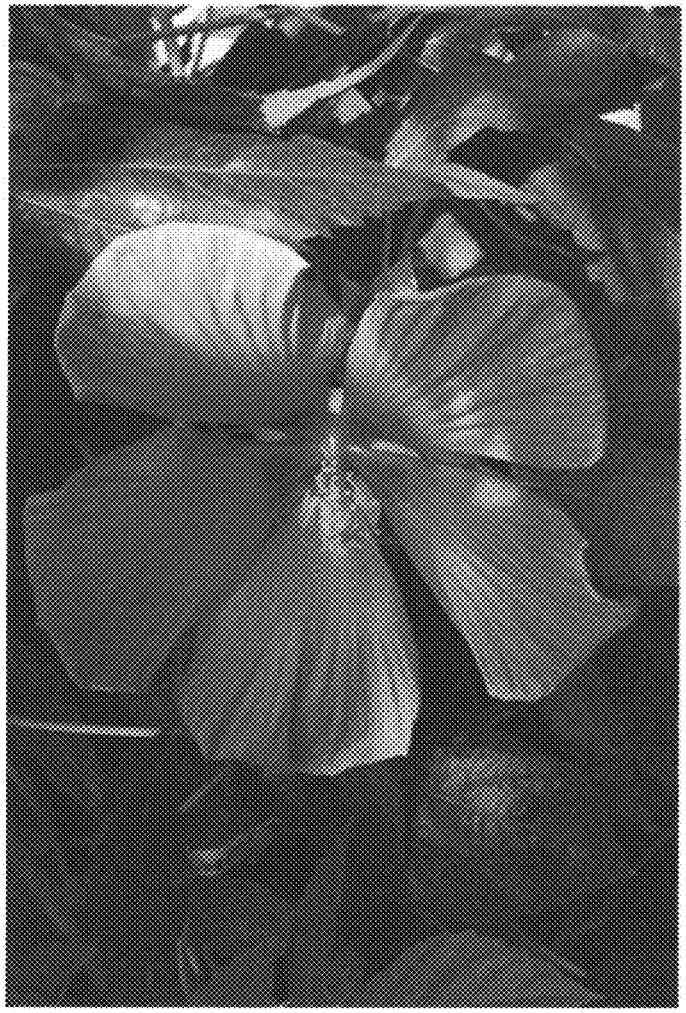
FIG. 3—Shows a '15173 GR' flower as seen looking slightly askew from the adaxial surface of the petals on a 2-year-old plant.
Figure 4:
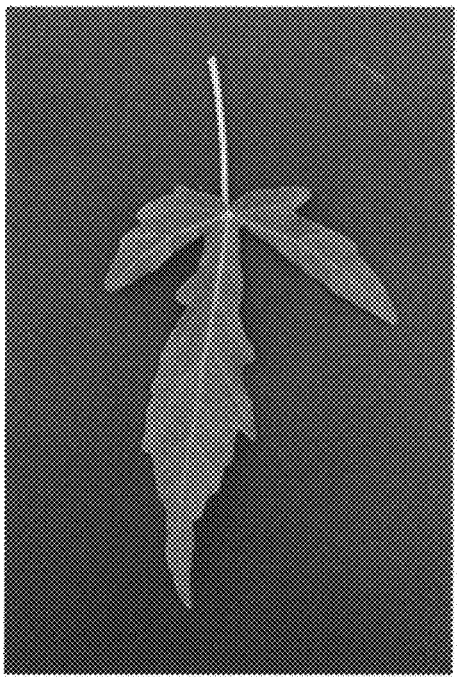
FIG. 4—Shows a '15173 GR' leaf that is representative of the most common shape.
Figure 5:
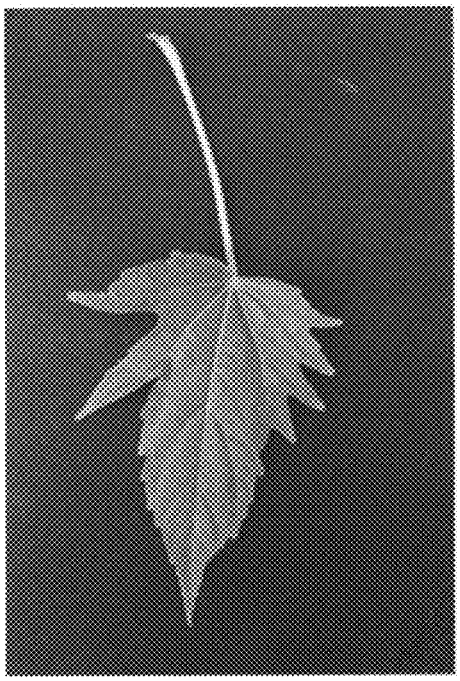
FIG. 5—Shows a '15173 GR' leaf that is representative the second most common shape.

The following detailed description sets forth the distinctive characteristics of '15173 GR'. The detailed description was obtained using two-year-old plants grown in loamy sand, open-field, full sun trials at a nursery near Vernon, Tex., during which the plants were supplemented with fertilizer and water as needed. These plants are natural habit and were not treated with plant growth regulators and they were not pinched at any time in the growth year. '15173 GR' has not been observed under all possible environments, and certain characteristics may vary slightly under different environmental conditions. Color references are to The Royal Horticultural Society Colour Chart of The Royal Horticultural Society of London (R.H.S.), 2001 ($4^{th}$ edition).

Propagation:

*Method*.—Stem cuttings.

*Time to initiate roots from stem cuttings after treating cuttings with a commercial rooting hormone*.—About 2 weeks under misting and at an air temperature of 85° C.

*Rooting habit*.—Normal, branching, fleshy, and developing a thick diameter (to about 2.5 cm).

*Root color*.—Pale yellow (between RHS 161D and RHS 162D), depending on soil type.

*Crop time* (*under normal summer growing conditions and when grown in a* 4 *L container from a rooted cutting*).—8 to 10 weeks to flower with very good plant vigor.

Plant:

*Plant shape and habit*.—Hardy herbaceous perennial with 8 to 12 moderately thick upright and heavily branched main stems producing an upright spreading mound about 100 cm tall and 90 cm wide, which is widest about 50 cm above the soil line.

*Primary branches*.—8 to 16 per main stem that protrude at about a 45° angle from horizontal.

*Lateral branches*.—On the middle half of the primary stems.

*Lateral branch size*.—Between 15 cm and 30 cm long (shorter at the upper nodes) and with an average diameter of 8.0 mm at their base.

*Flower location*.—Upper ⅓ of the plant beginning at axillary nodes while still developing at the apex.

*Stem*.—Rounded, glabrous, glaucous; averages about 100 cm tall and 2.5 cm diameter at their base.

*Stem color*.—Closest to moderate yellowish green (RHS 139D), lower parts of the stem have greenish reddish orange (RHS 174B) tint.

*Internode*.—About 16 nodes per stem below flower and about 30 total, average internode length about 4.5 cm of unpinched plant, but varies between 2.0 to 6.0 cm and are widest in middle portion of stem.

Foliage:

*Shape*.—Hastate, trilobed with indented margins.

*Texture*.—Adaxial and abaxial matte.

*Leaf blade size*.—To about 18.0 cm long and 10.0 cm wide, larger proximally and becoming smaller in distal portion of stem.

*Foliage color*.—Adaxial and abaxial moderate yellowish green (between RHS 137D and RHS 138A).

*Veins*.—Palmate; adaxial and abaxial veins moderate yellowish green (RHS 139D).

*Petiole size* (*average*).—5.0 cm long and 5.0 mm wide.

*Petiole color*.—Between moderate yellowish green (RHS 137D) and moderate orangish yellow (RHS 165C).

Flowers:

*Buds*.—One day prior to opening about 3.0 cm long and 2.5 cm in diameter, pointed apex and bluntly rounded base; and, prior to showing petals, about 3.5 cm long and 2.5 cm in diameter, ovoid with acute apex.

*Bud color*.—Exposed petal deep pink (between RHS 51B and RHS 52B); and, prior to showing petals, deep pink (RHS 52B).

*Epicalyx*.—Entire, smooth, puberulent both surfaces, linear with sharply acute apex and attenuate base, curved around sepals; typically 10 to 12 per flower; about 2.5 cm long tapering to base of about 3.0 mm wide.

*Epicalyx color*.—Adaxial and abaxial strong yellowish green (RHS 135C).

*Sepals*.—5, proximal half connate forming campanulate star-shaped calyx; acute apex; margin entire, edentate; puberulent abaxial glabrous adaxial; individually about 3.5 cm long and about 2.5 cm wide at fusion point. From the upper side of the flower, sepals visible as a star shape in the center of the flower.

*Sepal color*.—Abaxial and adaxial color strong yellowish green (RHS 135C).

*Flowers*.—Solitary, about 15 to 25 per main stem without pinching; primarily outwardly facing; average 17 cm across, larger in early part of flowering season; persist for one to two days, depending on temperature; effective for at least 14 weeks beginning early July and lasting into October (north Texas), no detectable fragrance.

*Petals*.—5; glabrous, slightly lustrous in the center and toward middle and perimeter, dull in the back, adnate to the androecium to form a column, not overlapping at any part. Veins: Parallelly veined, veins impressed on front and ribbed on back; vivid red (RHS 46B) extending from the eye zone to about the center of the petal, then fading to light pink (RHS 49C) from the center to the petal margin. Shape: Elongated.

Margins: Entire, edentate. Apex: Rounded. Base: Short claw-like. Surface: Adaxial and abaxial glabrous, slightly ribbed. Size (average): About 9.0 cm long and about 5.5 cm wide at widest portion; center dark eye about 3.0 cm diameter. Color: Adaxial and abaxial between moderate yellowish pink (RHS 38B) and strong pink (RHS 52D) in the mid and upper part, and between vivid reddish orange (RHS 44C) and deep yellowish pink (RHS 44D) from the middle part down to the edge of the center eye.

*Gynoecium*.—Style: enclosed in column about 7.5 cm long and 0.5 cm wide at base; column color vivid reddish orange (RHS 44C); style protruding from column and split in distal 10.0 mm portion into typically 5 branches, branch diameter 2.0 mm; branch color nearest strong pink (RHS 52D). Stigma: Typically 5; globose, puberulose, about 3.0 mm in diameter; color nearest strong pink (RHS 52D). Ovary: Superior, about 6.5 mm across at base and 6.0 mm tall; acute apex.

*Androecium*.—Filaments: Numerous, about 150; less than 1.0 mm in diameter and about 5.0 mm long; attached along nearly the entire length of column; color nearest pale purplish pink (RHS 62D). Anthers: Reniform; about 2 mm long and 1 mm wide; nearest light yellow (RHS 163D). Pollen: Numerous, globose, less than 0.1 mm long; color light yellow (RHS 163D).

*Pedicel*.—Rounded in cross section, finely puberulent; length from base of sepal to abscission point average 0.5 cm long and 4.0 mm wide; color brilliant yellowish green (RHS 135C).

*Peduncle*.—Rounded, puberulent, average about 3.0 cm long from abscission point to stem and 4.0 mm wide, slightly longer on earlier flowers.

*Peduncle color*.—Brilliant yellowish green (RHS 135C).

*Fruit*.—Few, loculicidal capsule; glabrous; globose, occasionally with abruptly acute apex; color between light yellowish brown (RHS 199C) and dark grayish yellow (RHS 199D) when mature.

*Seed*.—Minutely floccose, typically globose; about 3.0 mm in diameter; color between dark grayish reddish brown (RHS 200A) and moderate brown (RHS 200C).

Resistance: The plant grows best with plenty of moisture, but is able to tolerate some drought once established. Other pest and disease resistance beyond that of other hardy perennial *hibiscus* cultivars has not been observed. Hardiness at least from USDA Zone 4 through 9.

Commercial use: Suitable for potted plant culture, landscaping as a specimen or en masse, and especially suited for patios and confined spaces because of the compact habit.

What is claimed is:

1. A new and distinct *Hibiscus* hybrid (L.) plant named '15173 GR' as shown and described herein.

* * * * *